(12) United States Patent
Hansen

(10) Patent No.: US 6,770,046 B2
(45) Date of Patent: Aug. 3, 2004

(54) MINIMALLY INVASIVE EXTRICATION CERVICAL COLLAR

(76) Inventor: Kyle J. Hansen, 6839 Wellauer Dr., Wauwatosa, WI (US) 53213

(*) Notice: Subject to any disclaimer, the term of this patent is extended or adjusted under 35 U.S.C. 154(b) by 0 days.

(21) Appl. No.: 10/282,613

(22) Filed: Oct. 29, 2002

(65) Prior Publication Data
US 2004/0082893 A1 Apr. 29, 2004

(51) Int. Cl.[7] .................................................. A61F 5/00
(52) U.S. Cl. ................................. 602/18; 128/DIG. 23
(58) Field of Search ............................... 602/18, 16, 17, 602/5; 128/DIG. 23, 845

(56) References Cited

U.S. PATENT DOCUMENTS

| | | | | |
|---|---|---|---|---|
| 2,801,630 A | * | 8/1957 | Moore | 602/18 |
| D188,302 S | | 6/1960 | Monfardini | |
| 3,027,894 A | * | 4/1962 | Moore | 602/18 |
| 3,042,027 A | * | 7/1962 | Monfardini | 602/18 |
| 3,075,521 A | * | 1/1963 | Grassl | 602/18 |
| 3,135,256 A | | 6/1964 | Gruber | |
| 3,220,406 A | * | 11/1965 | Connelly | 602/18 |
| 3,916,885 A | * | 11/1975 | Gaylord, Jr. | 602/18 |
| 4,099,523 A | * | 7/1978 | Lowrey | 602/18 |
| 4,543,947 A | | 10/1985 | Blackstone | |
| 4,827,915 A | * | 5/1989 | Gorsen | 602/18 |
| 4,886,052 A | * | 12/1989 | Calabrese | 602/18 |
| 5,180,361 A | * | 1/1993 | Moore et al. | 602/18 |
| 5,593,382 A | * | 1/1997 | Rudy et al. | 602/18 |
| 5,788,658 A | | 8/1998 | Islava | |
| 5,797,713 A | * | 8/1998 | Tweardy et al. | 411/339 |
| 6,423,020 B1 | * | 7/2002 | Koledin | 602/18 |

FOREIGN PATENT DOCUMENTS

DE 3318938 11/1984

* cited by examiner

Primary Examiner—Nicholas D. Lucchesi
Assistant Examiner—Huong Q. Pham
(74) Attorney, Agent, or Firm—Ryan Kromholz & Manion, S.C.

(57) ABSTRACT

A minimally invasive, adjustable cervical collar including a collapsible occipital section. The collar may be placed on a patient requiring immobilization of the neck without moving the patient's head or the patient's neck. The collar includes an adjustable occipital section and a mandibular support section. The device may be of unitary, one-piece construction or the occipital and mandibular sections may be separate, yet attachable.

10 Claims, 11 Drawing Sheets

MINIMALLY INVASIVE EXTRICATION CERVICAL COLLAR

BACKGROUND OF THE INVENTION

The present invention relates to cervical collars, specifically, cervical collars designed for immobilization of the spine and neck in emergency medical situations. Immobilization of the spine is critical before transporting an injured person to a hospital. Immobilizing cervical collars assist in preventing movement of the neck, which may in fact result in paralysis or even death of a person with a spinal injury.

The current art is such that many immobilization or extrication cervical collars are single piece designs that are not adjustable for the posterior or occipital section, nor are they easily or safely applied to an injured person. One problem with the current art is the height of the occipital section of the collar. Many collars are simply too tall for all individuals relative to each individual's neck and head. Because of this excess height, it is often necessary for emergency medical personnel to elevate an injured person's head in order to accommodate the collar when placing the occipital section of the collar beneath a person's neck. Though the movement may be minimal, any movement whatsoever of a person's neck may be detrimental for a person with an injured spine.

Another problem with commercially available devices is that cervical immobilization collars are often designed such that they can be placed beneath a patient's neck from only one direction, usually from the right side of a patient's head. Furthermore, there may be unavoidable logistical situations such as little room to work on one side of the patient, the presence of an obstruction on one side of the patient, the patient's position, etc. These situations can present numerous problems, raising the likelihood that it will be necessary to move the patient's head in order to properly place the collar.

It is common in the art to construct cervical collars that are designed for reuse as well as collars that are disposed of after a single use. In either instance, the majority of prior art collar designs are not "one size fits all," resulting in the need for emergency personnel to carry several sizes of collars with them. In the case of a disposable collar, an inappropriately sized collar may be placed on a patient before it is determined that the selected collar is the wrong size. The application and removal of incorrectly sized collars multiple times presents an opportunity for accidental exacerbation of a present injury or the creation of a new injury during each application and removal process. This also results in the needless disposal of multiple collars for a single patient.

For instance, U.S. Pat. No. 6,423,020 (Koledin) describes a cervical collar that can be adjusted to immobilize a patient's head. The novelty of the invention resides in the adjustable chin support member. The Koledin reference also discloses an adjustable occipital section. However, it is important to note that the adjustable occipital section must be adjusted and locked in place with a separate pin prior to applying the collar to the patient. Furthermore, it is apparent that the occipital section does not collapse to approximately one-half of its fully extended height. As in the prior art, when applying the Koledin collar an emergency worker may be required to move the patient's neck to fit the relatively wide occipital section beneath a patient's neck. There will be some movement of the patient's neck as the vertical height of the occipital section is larger than the open area formed between the patient's head and shoulders and curve of the patient's neck. While this may only require a small movement of the patient's neck, it may be enough of a movement to exacerbate a potential injury or cause further injury or trauma to the patient.

Therefore a need exist for a cervical collar that may be applied with minimal movement of the patient's neck while providing solid support to the occipital portion of a patient's neck before a patient is moved or transferred from an emergency site.

SUMMARY OF THE INVENTION

The present invention seeks to address the shortcomings in the current art. The cervical collar of the present invention includes two separate and distinguishable sections: an occipital section and a chin, or mandibular, section. The occipital section is collapsible, and may be properly placed from either the left or the right side of the injured person's head and neck in its collapsed state by sliding it beneath the person's neck. No lifting of the person's head is required. Once the collapsed occipital section is in place, draw straps on the occipital section are employed to pull the occipital section into an expanded position and to secure it in place, thereby providing a solid support for the patient.

The mandibular section may be connected to the occipital section forming a unitary or one-piece cervical collar. Alternatively, the mandibular section may be designed as a separate, yet attachable piece. Once the occipital section is secured in place, the mandibular section encircles the front of the patient's neck and is secured to the occipital section, preferably with a hook and loop material, such as Velcro®. The secured collar will allow the patient to be moved from an emergency site with minimal movement of the patient's neck and spine thereby preventing exacerbation of present injuries as well as minimizing the likelihood of further injury to the patient.

DETAILED DESCRIPTION

Although the disclosure hereof is detailed and exact to enable those skilled in the art to practice the invention, the physical embodiments herein disclosed merely exemplify the invention which may be embodied in other specific structures. While the preferred embodiment has been described, the details may be changed without departing from the invention, which is defined by the claims.

Figure 1:
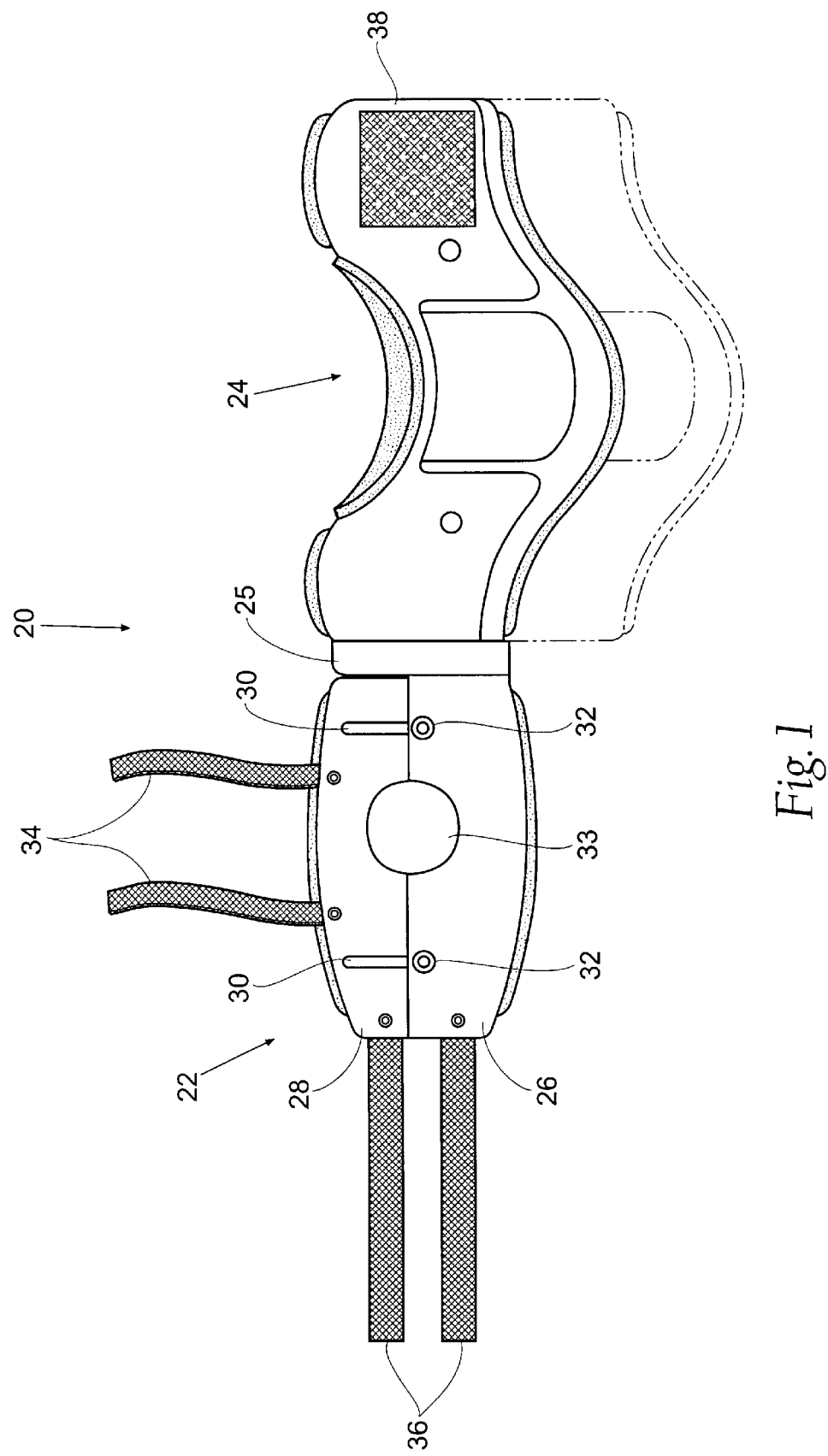
FIG. 1 is a front view illustrating a first embodiment of a cervical collar according to the present invention.

FIG. 1 shows a front view of an embodiment according to the present invention. A cervical collar 20 is shown having an occipital section 22 and a mandibular section 24. The collar 20 is formed from a flexible, semi-rigid material, such as plastic. The occipital section 22 is connected to the mandibular section 24 at an end tab 25. The end tab 25 may be integrally formed with the mandibular section 24, or designed from a separate piece of material. The mandibular section 24 may be adjustable (as represented in phantom) to accommodate varying sizes of necks.

Still referring to FIG. 1, the occipital section 22 has a first band 26 and a second band 28. The first band 26 is connected to the end tab 25. The second band 28 is slidably connected to the first band 26 and the end tab 25. In the preferred embodiment, the first band 26 and the second band 28 are of relatively the same horizontal width, sufficiently wide enough to allow the occipital section 22 to firmly support a patient's neck. Again in my preferred embodiment, the vertical heights of the first band 26 and of the second band 28 are also relatively the same. A pair of slots 30 is formed in the second band 28. The slots 30 are in communication with a pair of posts 32 that are connected to the first band 26. The slots 30 and the posts 32 allow the second band 28 to be slidably collapsed and expanded with respect to the first band 26 and to the mandibular section 24. When the occipital section 22 is in an expanded position, an opening 33 is formed between the first band 26 and the second band 28. The opening 33 allows for proper positioning of the patient's head and makes wearing of the collar 20 more comfortable for the patient.

Figure 1A:
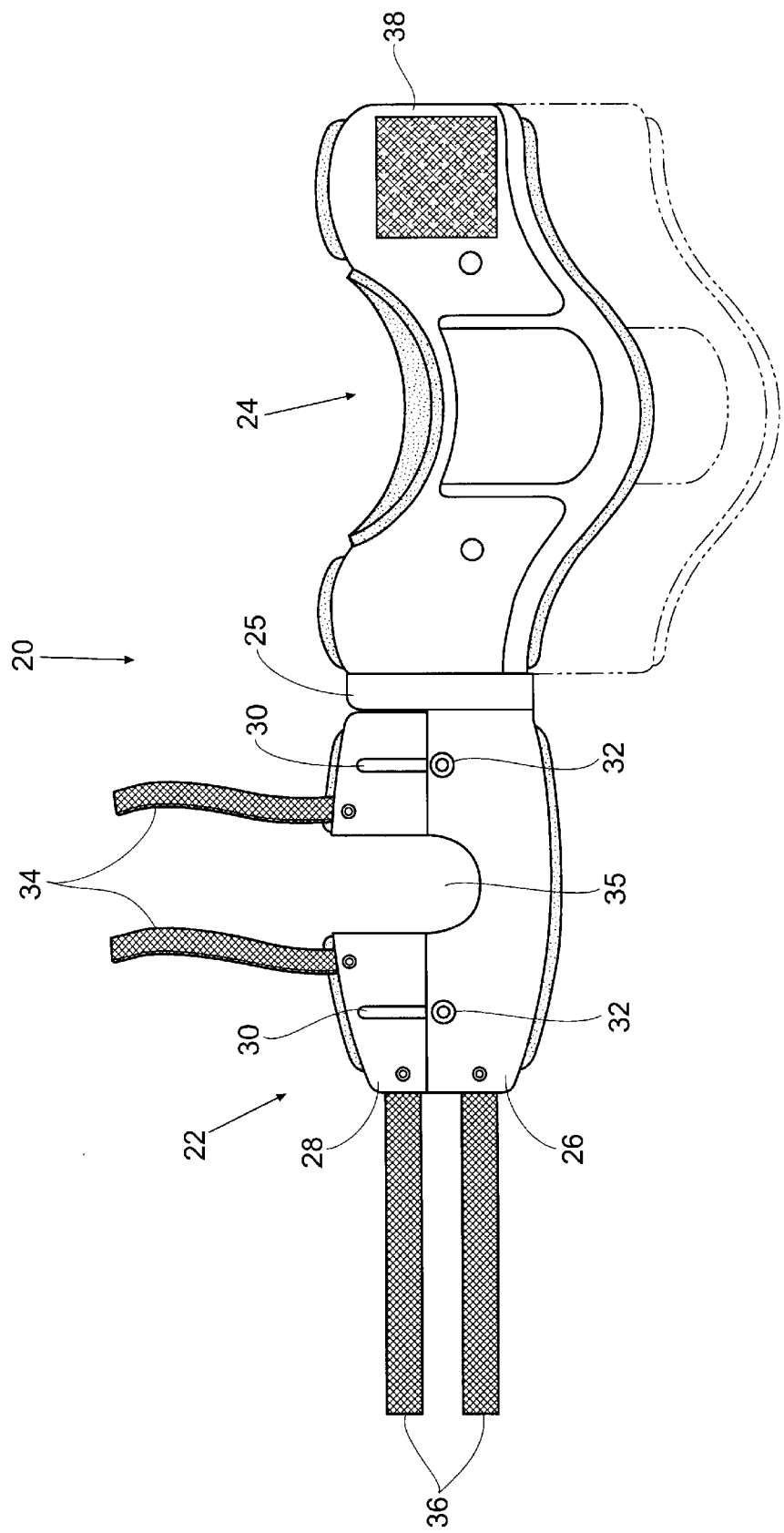
FIG. 1A is a front view illustrating an alternative first embodiment of a cervical collar according to the present invention.

Now referring to FIG. 1A, an alternative embodiment of the collar 20 is shown. Opening 33 has been replaced with "U" shaped or elongated channel 35. As will be discussed in detail below, the presence of "U" shaped channel 35 allows the occipital section 22 to be expanded without any disturbance or movement of the patient's head.

A pair of pull straps 34 is connected to the second band 28 to assist in collapsing and expanding the occipital section 22. While it is possible to adjust the occipital section 22 without the use of the pull straps 34, or other adjustment aids, the use of the straps 34, allows for the least amount of movement of a patient's neck, thereby reducing the chance of further aggravating any possible injuries.

Still referring to FIGS. 1 and 1A, the collar 20 is capable of securely encircling a patient's neck. A pair of adjustable supporting fasteners 36 is located on the occipital section 22, opposite where the occipital section 22 is connected to the mandibular section 24. The fasteners 36, preferably located with one fastener 36 on the first band 26 and one fastener 36 on the second band 28, are employed together with a fastening material 38 to adjust the cervical collar 20 and secure the collar 20 in place when encircled around a patient's neck. The adjustable fasteners 36 and fastening material 38 are preferably designed of a hook and loop style material, such as Velcro®. While the collar 20 is shown with two fasteners 36, it is to be understood that additional or fewer fasteners could be used without departing from the present invention.

Figure 2:
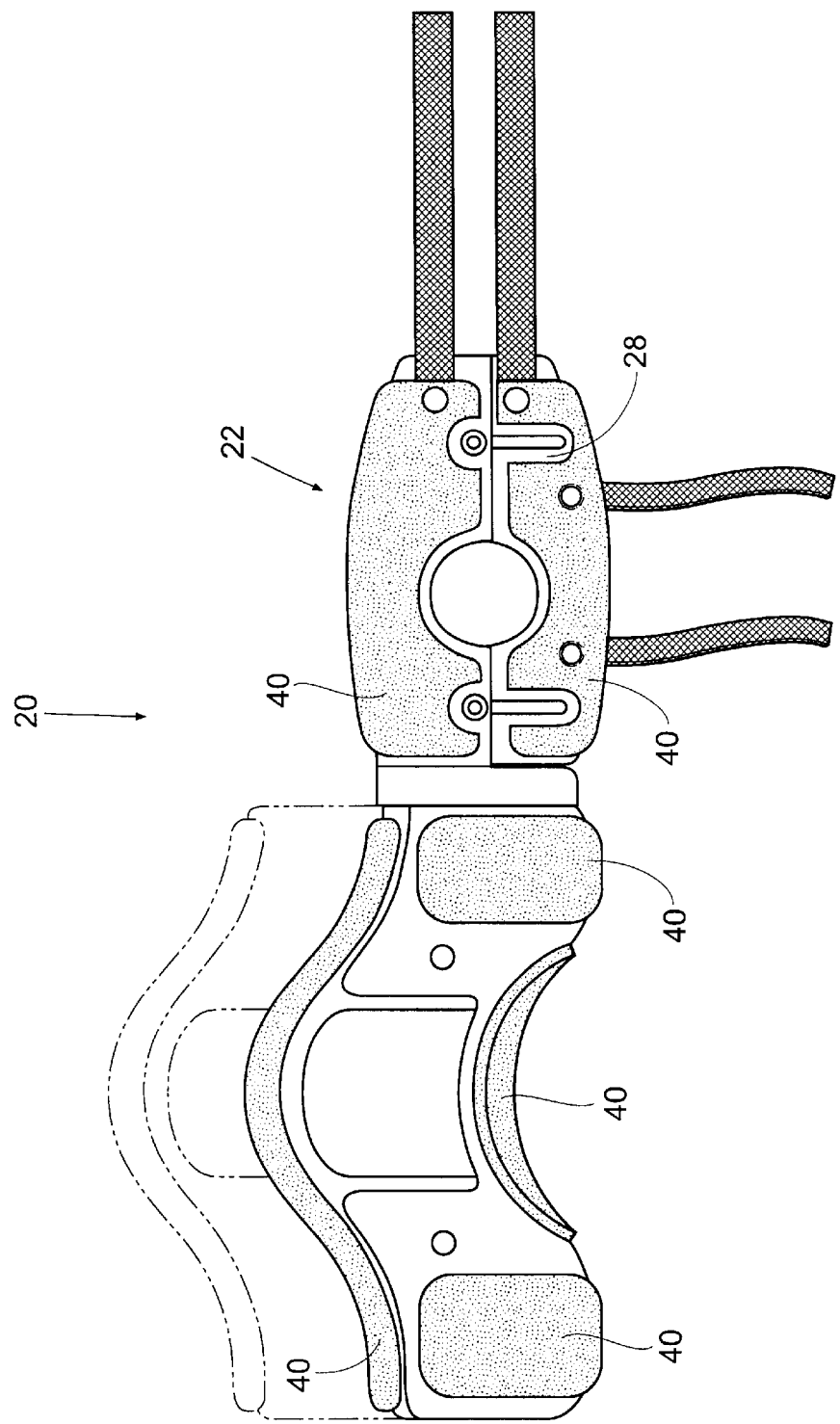
FIG. 2 is a back view of the embodiment shown in FIG. 1.

FIG. 2 shows the backside of the cervical collar 20. Padding 40 is attached to the collar 20 in areas where the collar 20 directly contacts the patient, such as the shoulder, chin, neck, and chest areas. The padding 40 can be a foam type material, or any similar material that will contribute to the comfort of the patient wearing the collar 20. The padding 40 on the occipital section 22 is arranged in such a way that the second band 28 will be allowed to slide uninhibitedly with relation to the first band 26, while still solidly supporting a patient's neck.

In FIG. 2, the first band 26 and the second band 28 are situated parallel to one another and preferably overlap in a substantially planar relationship. However, it has been contemplated that the bands may be arranged to abut one another in the same plane. Likewise, the bands may have an arcuate shape that more closely fits the shape of the patient's neck.

Figure 2A:
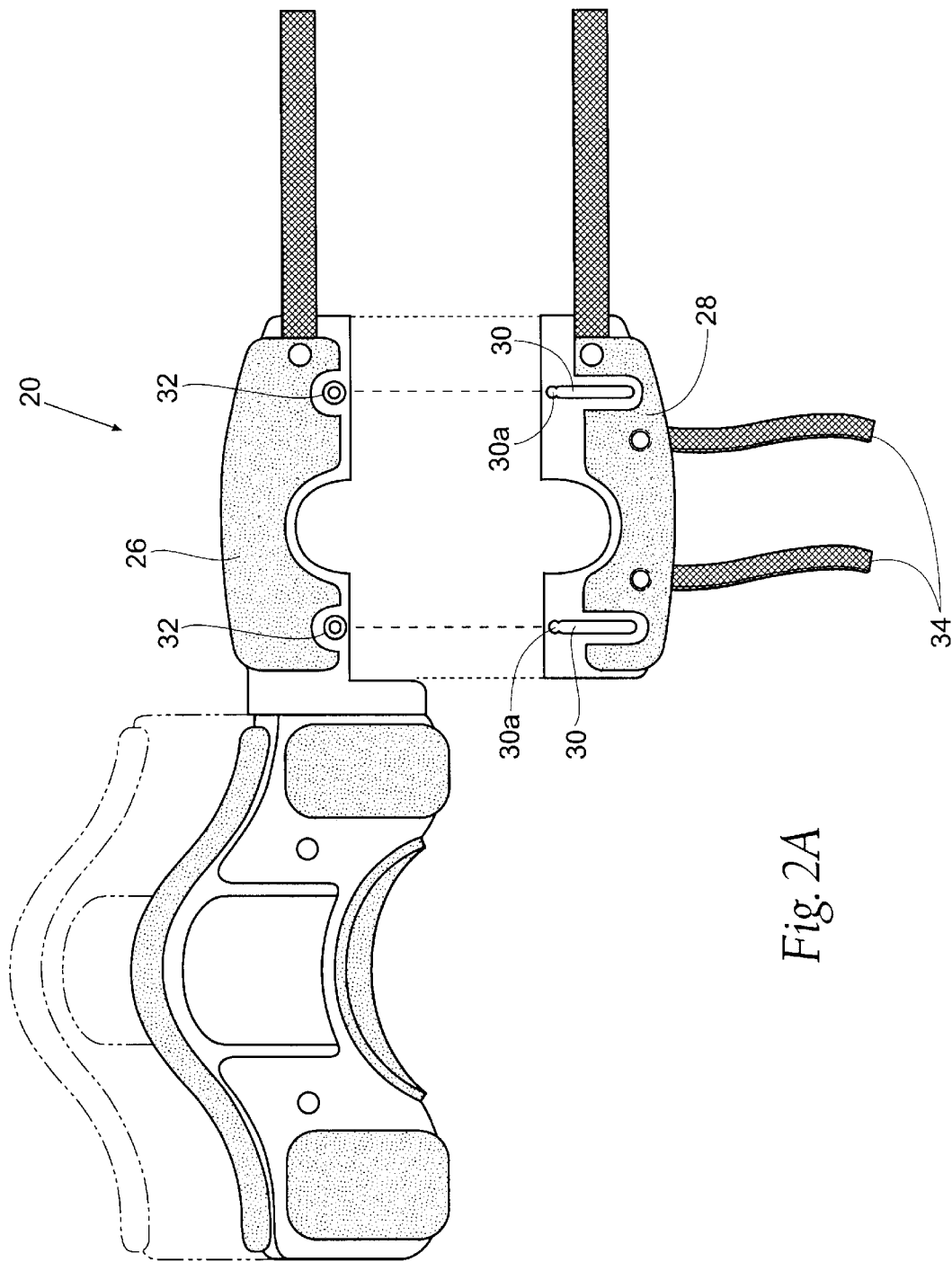
FIG. 2A is an exploded back view of the embodiment shown in FIG. 1.
Figure 7:
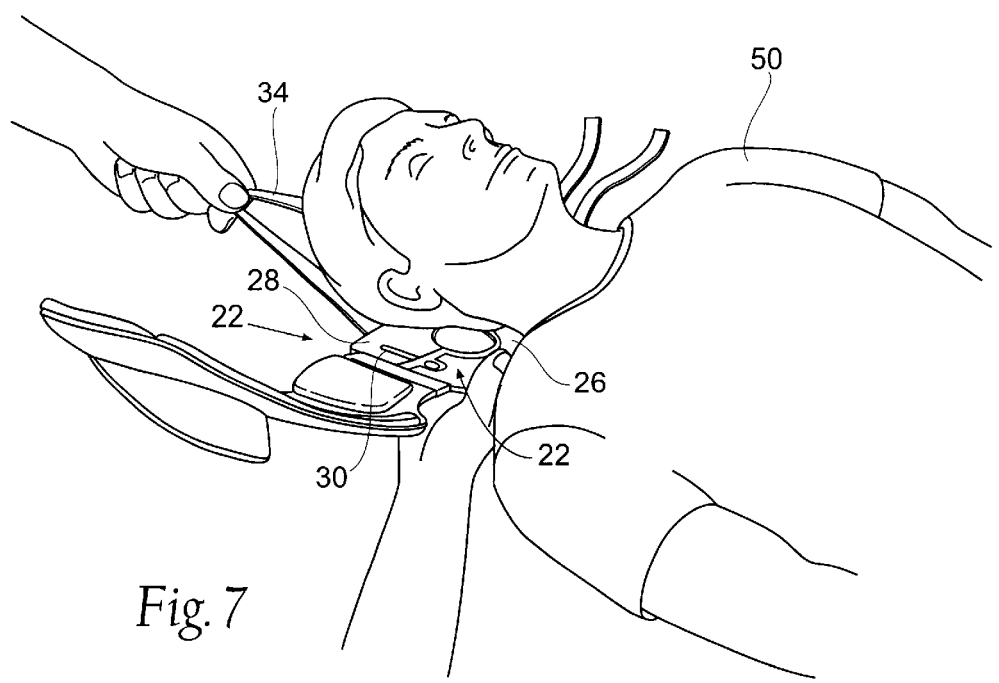
FIG. 7 shows the height of the occipital section being adjusted.

FIG. 2A is an exploded back view of the cervical collar 20 shown in FIG. 1. The occipital section 22 is exploded to show the first band 26 separately from the second band 28. The slots 30 each have a biased end 30a. As the occipital section 22 is expanded, the posts 32 slide along the slots 30, and the posts 32 will come into contact with the biased end 30a of the slots 30. The slots 30 act as a guide so that the first band 26 and the second band 28 are restricted from movement laterally with respect to one another. An emergency worker will further expand the occipital section 22 past the indent forming the biased end 30a by pulling on the pull straps 34 (see FIG. 7), thereby fixing and securing the occipital section 22 in place. Other means, such as snaps or locks, could also be used to hold the occipital section 22 in place when extended. However, the use of the biased end 30a ensures the least amount of movement for a patient's head and neck, as no extra movement is necessary to snap or lock the collar in place.

Figure 3:
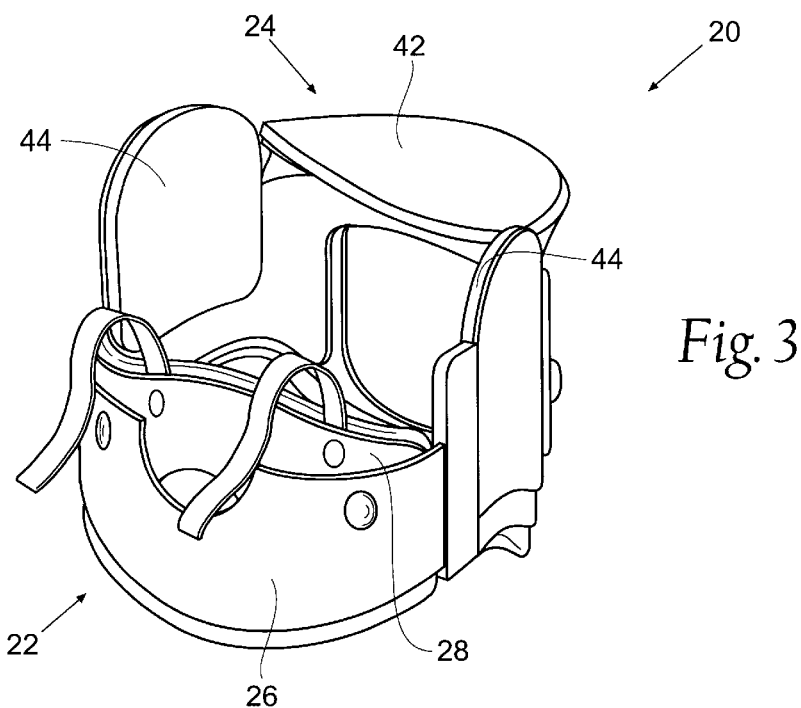
FIG. 3 is a perspective view of the present invention showing the occipital section in a collapsed position.

Referring to FIG. 3, a perspective view of the collar 20 is shown in an enclosed position. When the collar 20 is enclosed by connecting the hook and loop fastener and material 36 and 38 (not shown), areas of the mandibular section 24, such as a chin support 42 and neck side rests 44, as they conform to the patient become more evident. The chin support 42 and the side rests 44 contribute to the immobility features of the collar 20. The occipital section 22 is shown in a collapsed position, with the second band 28 sliding behind the first band 26.

Figure 4:
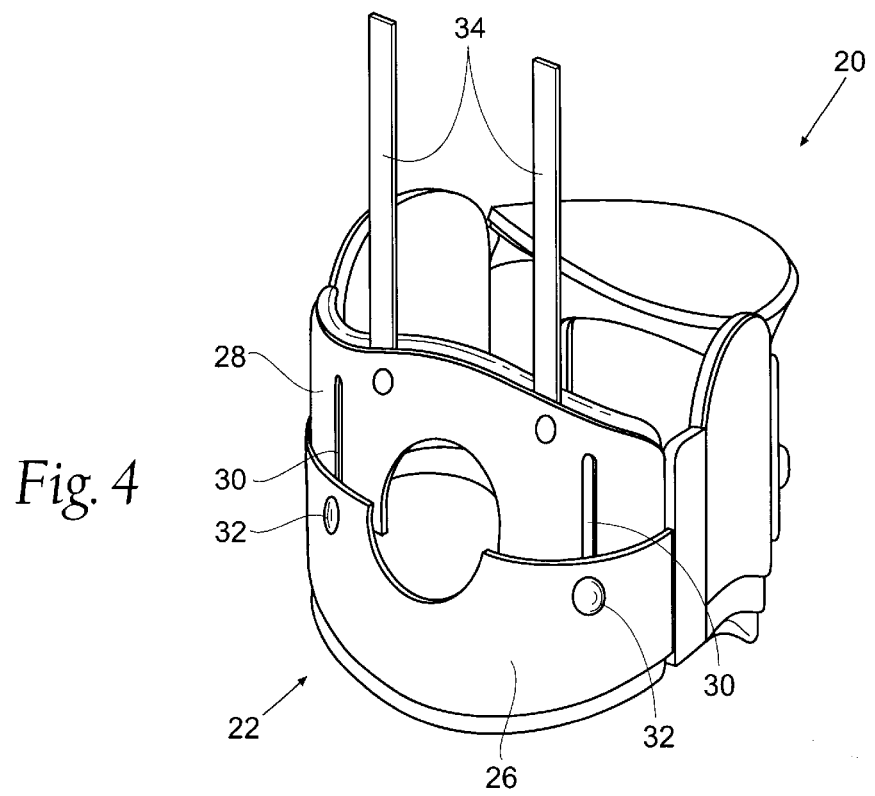
FIG. 4 is a perspective view of the present invention showing the occipital section in an expanded position.

FIG. 4 shows the same perspective view of the collar 20 as seen in FIG. 3 except that the occipital section 22 is now shown in an expanded position. The straps 34 are pulled upwardly to move the second band 28 out from behind the first band 26. The second band 28, which is approximately the same height as the first band 26, is pulled outwardly and secured in a fully extended position. The biased end 30a of the slots 30 (see FIG. 2A) indicate when the occipital section 22 has been fully extended. Also, the biased ends 30a of the slots 30 allow the posts 32 to hold the occipital section 22 in an extended position. It is also possible that the posts 32 may contain a locking mechanism that will further secure the occipital section 22 in place when extended.

Figure 5:
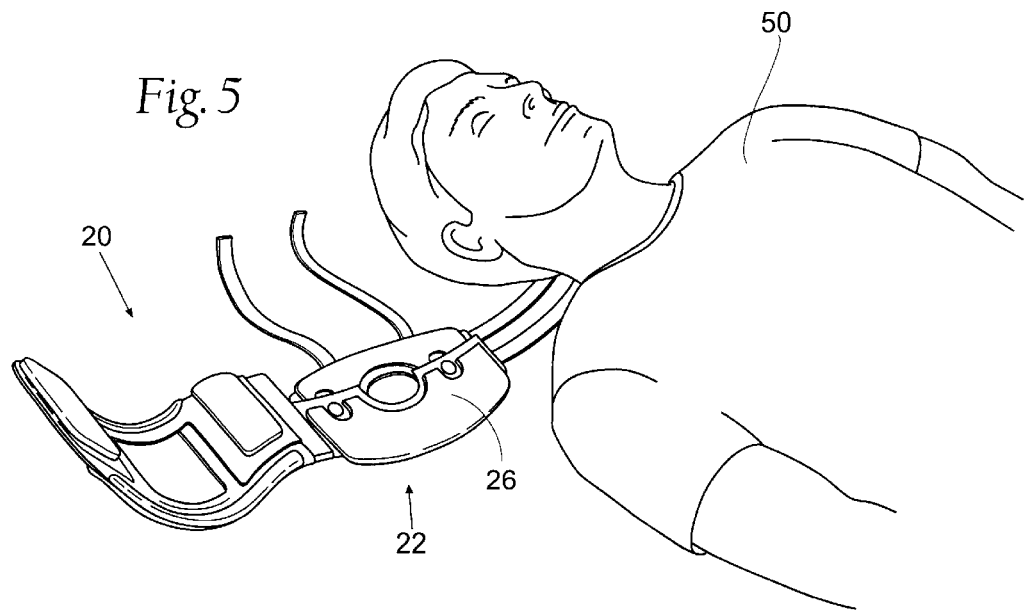
FIG. 5 shows the invention being slid beneath a patient's neck.
Figure 6:
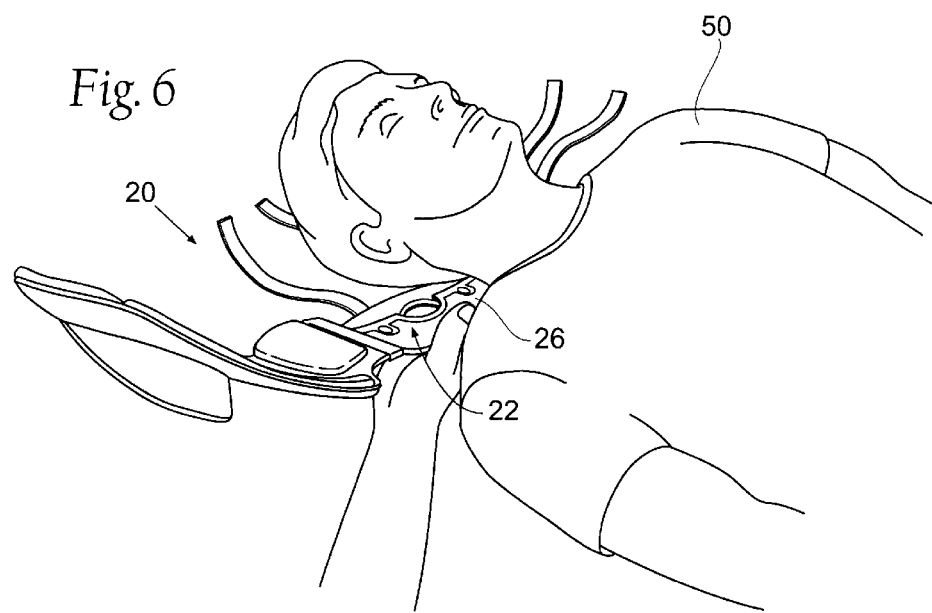
FIG. 6 shows the invention positioned beneath a patient's neck.

FIGS. 5 and 6 show the collar 20 in relationship to a patient 50. As the patient 50 lies unmoving, the collapsed occipital section 22 is slid underneath the patient's neck. The occipital section 22 can fit comfortably beneath the patient's neck without needing to adjust or move the patient's neck. Also, because the occipital section 22, when collapsed, is narrower than the space between the patient's head and shoulders, the collar 20 may be positioned properly while the occipital section 22 is beneath the patient's neck without moving the patient, thereby allowing an emergency worker to properly position the collar 20. The result is less of a chance of aggravating any present injury and, also, reducing the chance of further injury. Once the collar 20 is situated adequately underneath the neck, an emergency worker will hold the first band 26 of the occipital section 22 in place. The worker than uses her other hand to pull on the pull straps 34 to extend the second band 28 of the occipital section 22 (see FIG. 7). The posts 32 connected to the first band 26 slide along the slots 30 of the second band 28 until the occipital section 22 is fully extended. The biased ends 30a of the slots 30 (see FIG. 2A) indicate full extension of the occipital section 22, thus forming a solid support for the patient's neck.

Figure 8:
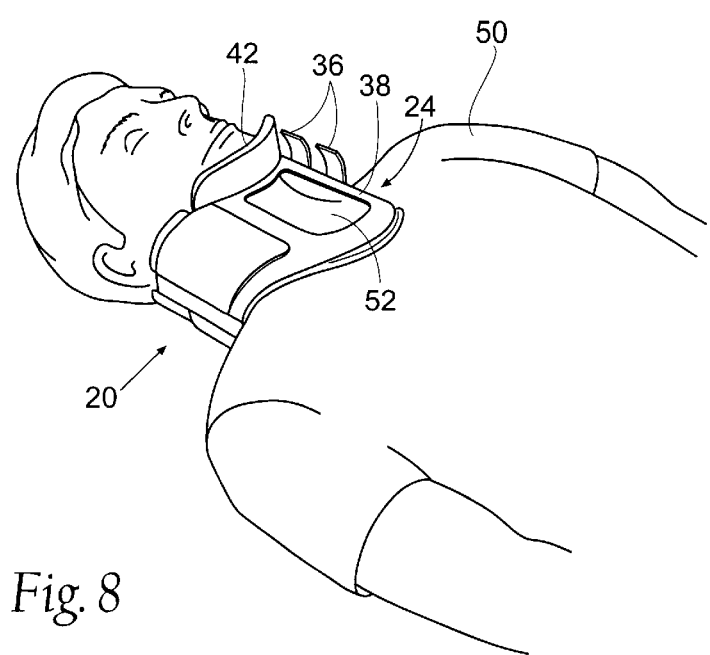
FIG. 8 shows the invention secured around a patient's neck.

As shown in FIG. 8, the collar 20 may now be wrapped around the patient's neck. The chin rest 42 of the mandibular section 24 is fit below the patient's chin and the collar 20 is secured by connecting the adjustable loop fasteners 36 to the hook material 38. The chin rest 42 may be adjusted for the size of the patient's neck, if necessary. A hole 52 is shown in the mandibular section 24 of the collar. While not necessary for the invention, the hole 52 allows access to a patient's throat, if, for example, an emergency tracheotomy must be performed. The hole 52 may also make wearing of the collar 20 more comfortable for the patient 50.

Figure 9:
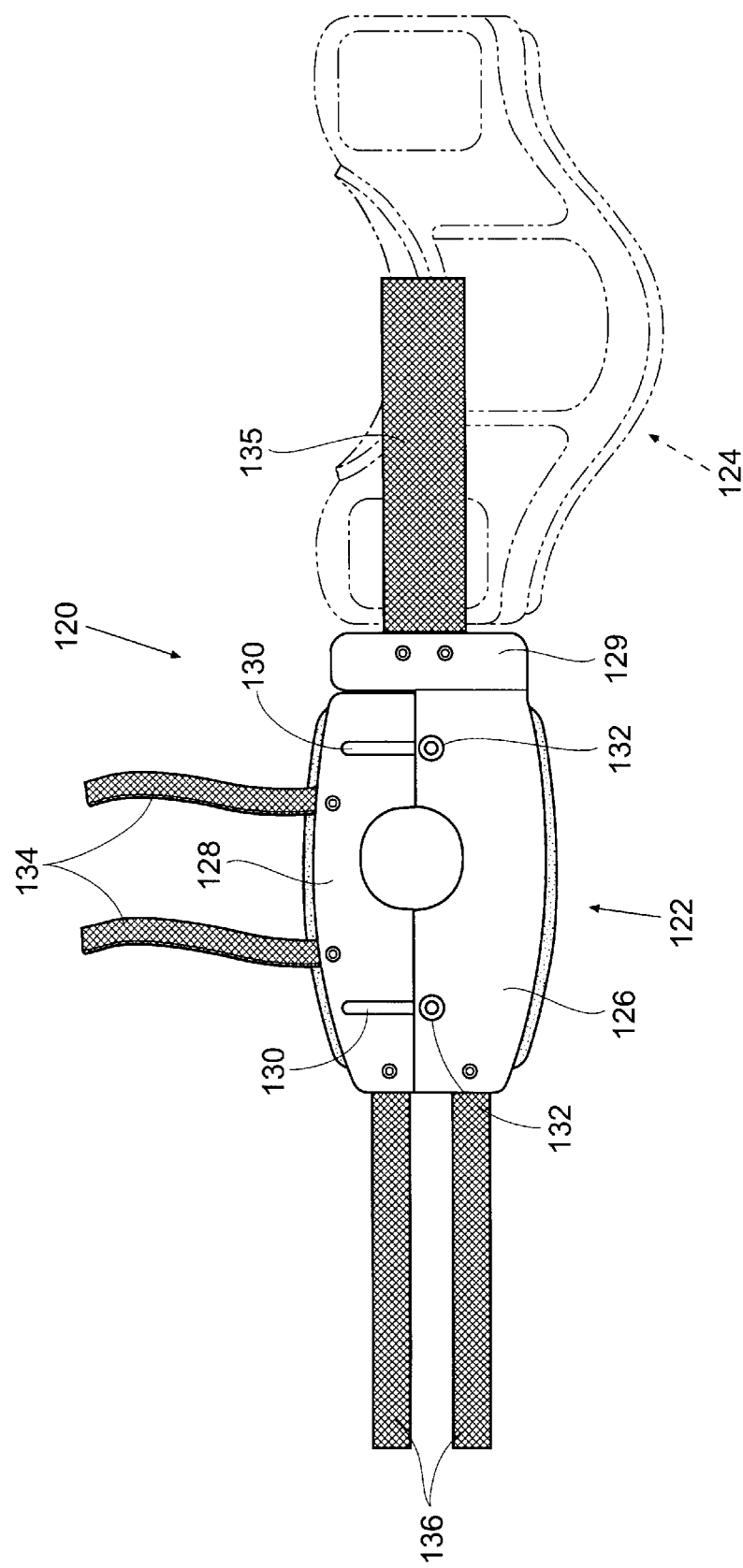
FIG. 9 is a front view of a second embodiment of the present invention.

FIG. 9 shows an overhead view of a second embodiment of the present invention. A cervical collar 120 is formed of an occipital section 122 and a mandibular section 124 (shown in phantom). The occipital section 122 is separate and distinct from the mandibular section 124. The occipital section 122 has a first band 126 and a second band 128. The first band 126 is fixedly secured at one end to an end tab 129. The second band 128 is slidably connected to the end tab 129. While the embodiment is shown with one end tab, it would be possible to have an end tab on either side, or no end tab at all. The use of one end tab gives the invention added support while still allowing the occipital section to be easily maneuverable without having to move a patient's neck.

Still referring to FIG. 9, the second band 128 contains a pair of slots 130, which are in communication with a pair of posts 132 that are connected to the first band 126. The slots 130 and the posts 132 allow the second band 128 to be collapsed and expanded with respect to the first band 126 and to the end tab 129. A pair of pull straps 134 is connected to the occipital section 122 to assist in collapsing and expanding the second band 128. A hook and loop, or Velcro® material, adjustable supporting fastener 135 is attached to the end tab 129. A pair of adjustable fastening strips 136 is located on the end of the occipital section 122 opposite the end tab 129. The pair of strips 136 is made of the same material as that of the fastener 135. The number of adjustable fastening strips 136 is not determinative of the invention. Also, the adjustable fastener 135 could be designed as two or more narrower fasteners.

Figure 10:
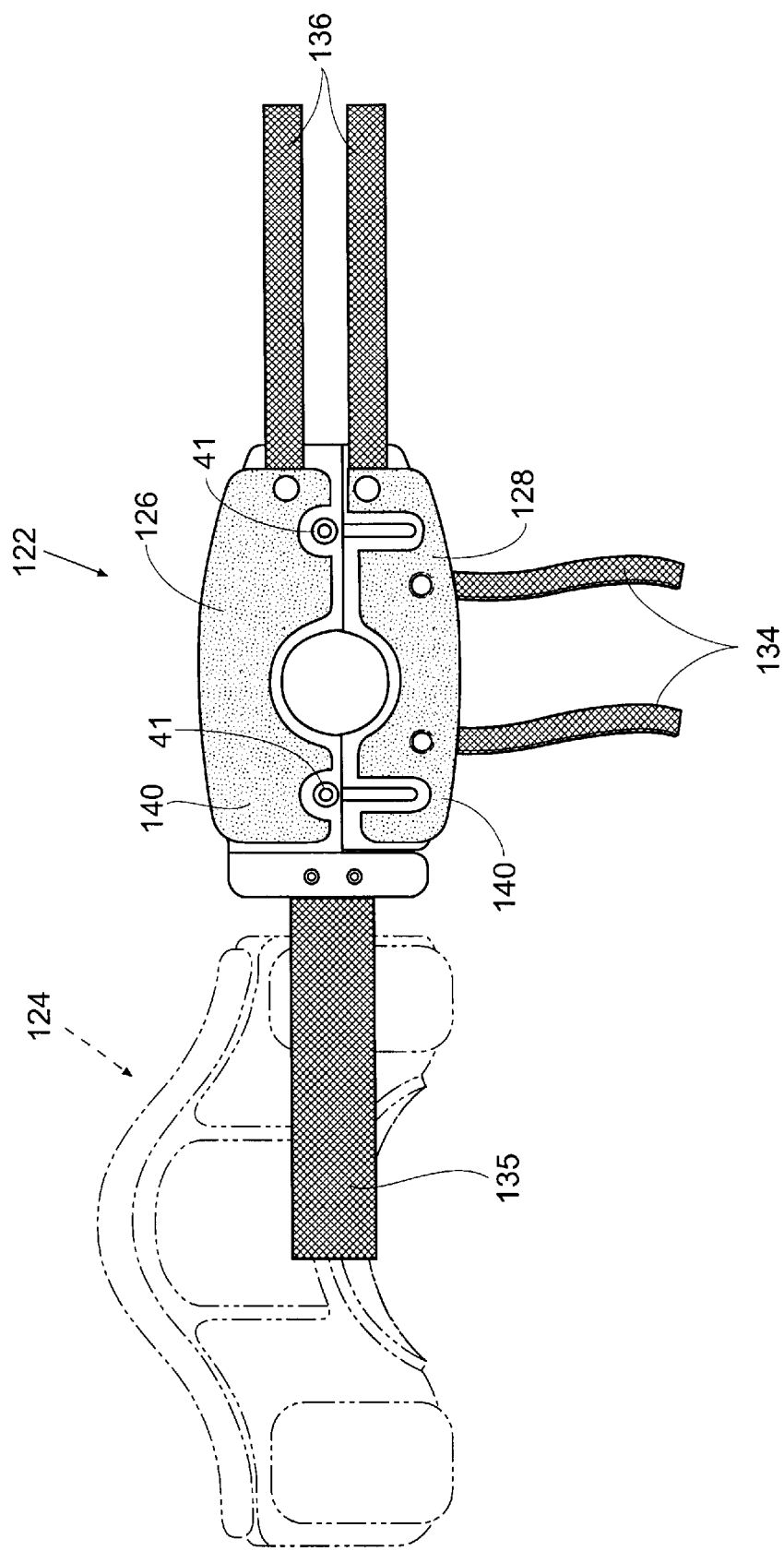
FIG. 10 is a back view of a second embodiment of the present invention.

FIG. 10 shows the backside of the occipital section 122 shown in FIG. 9. Padding 140 is attached to the occipital section 122 on areas where the occipital section 122 will be in direct contact with a patient. The padding 140 on the occipital section 122 is attached to both the first band 126 and the second band 128 in such a way that the second band 128 will be allowed to slide uninhibitedly with relation to the first band 126 while still supporting a patient's neck. Similar to FIG. 2A, the slots 130 have a biased end 130a (not shown), which indicates when the occipital section 122 is in the fully expanded position.

Figure 11:
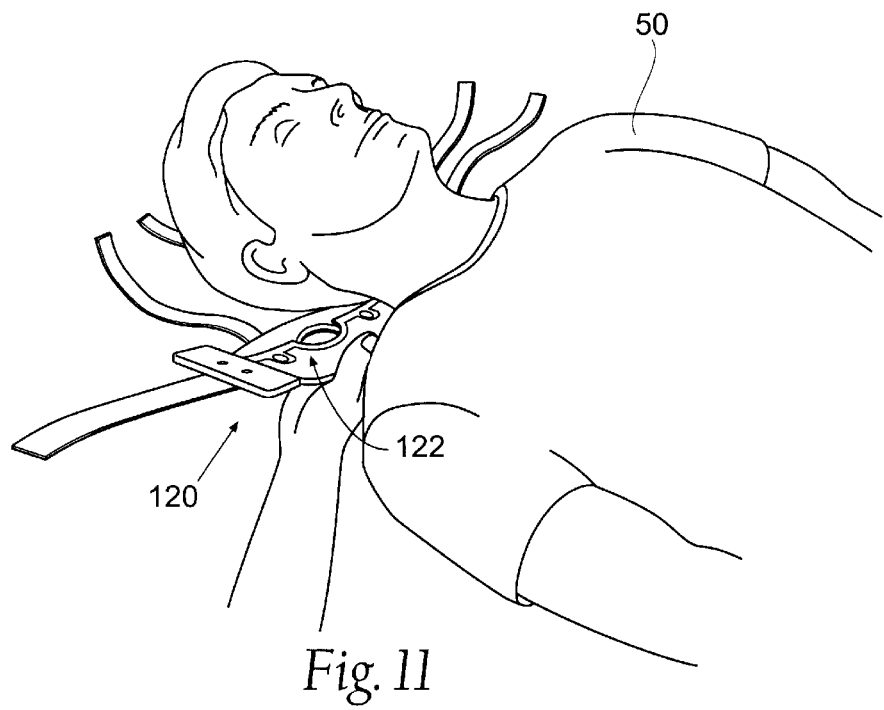
FIG. 11 shows the second embodiment of the present invention positioned beneath a patient's neck.

FIG. 11 shows the occipital section 122 in relation to the patient 50. The collapsed occipital section 122 is slid under the patient's neck. The occipital section 122 can fit comfortably underneath the patient's neck without adjusting or moving the patient's head or neck. This results in less of a chance of aggravating any present injury and also reduces the chance of further injury. Also, since the occipital section 122 is detached from the mandibular section 124 (not shown), the occipital section 122 may be slid underneath the patient's neck from either side. This is especially important when the patient may be lying in such a position, such as on a hillside, that placement of the occipital section 122 from a specific direction is prohibited by the ground. The chance that a patient's neck may be unnecessarily moved is reduced by this safety features of the collar 120.

Figure 12:
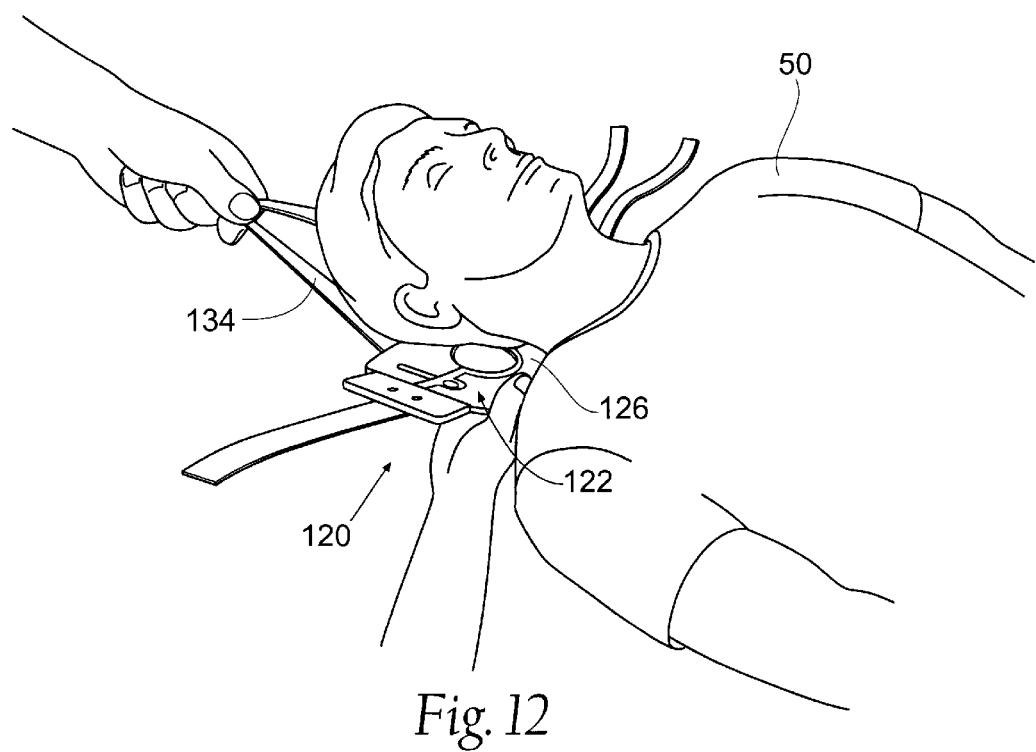
FIG. 12 shows the height of the occipital section of the second embodiment being adjusted.

As shown in FIG. 12, once the occipital section 122 is centered in place, an emergency worker grasps the first band 126. If necessary, the occipital section 122 can be further centered by pulling on the fastener 135 and the strips 136. The worker then grabs and pulls the pull straps 134 until the occipital section 122 is in a fully expanded position. Once extended, the occipital section 122 forms a solid support for the patient's neck.

Figure 13:
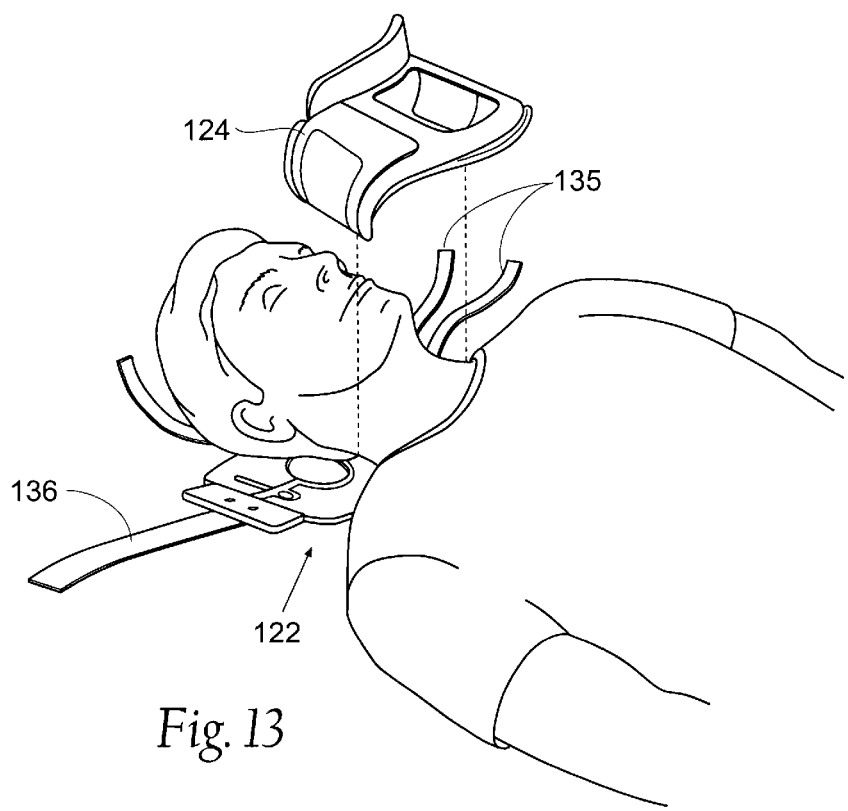
FIG. 13 is an exploded view of the second embodiment of the present invention.

As shown in FIG. 13, the mandibular section 124 may now be placed on the patient's neck. A chin rest 142 of the mandibular section 124 is fit below the patient's chin. The mandibular section 124 is then secured to the occipital section 122 on one side by the adjustable fastener 136 and on the other side by the adjustable fastening strips 135. The fastener 136 and the strips 135 can be designed to connect to hook material located on the mandibular section 124, or they can be designed to loop through slits in the mandibular section and folded back on themselves.

Figure 14:
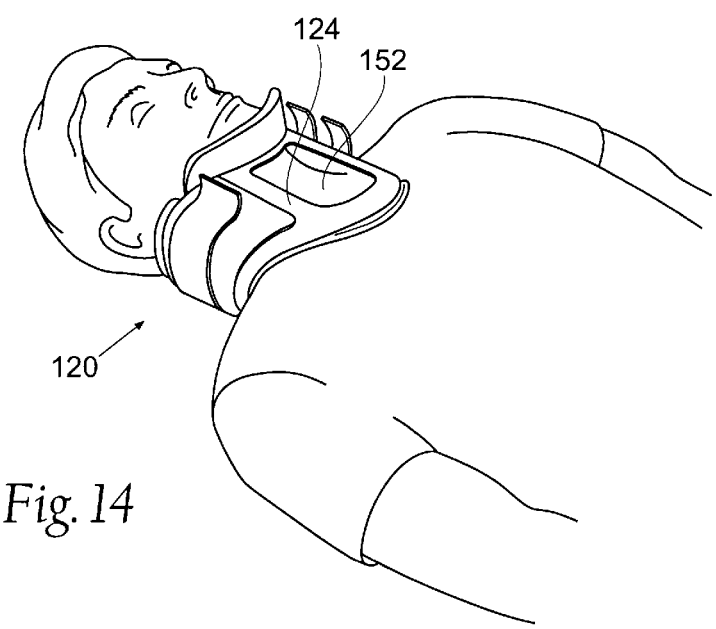
FIG. 14 shows the second embodiment of the present invention secured around a patient's neck.

In FIG. 14, the collar 120 is shown secured around the neck of the patient. A hole 152 is shown in the mandibular section 124 of the collar 120. While not necessary for the invention, the hole 152 allows access at a patient's throat, if, for example, an emergency tracheotomy must be performed. The hole 152 may also make wearing of the collar 120 for more comfortable for the patient 50.

The adaptability of the occipital section reduces possible injuries to a patient. For instance, the first band of the occipital section is described as being held securely in place while the second band is slidable. It is possible and contemplated to fall within the scope of the present invention for the first band to slide and the second band to be held in place, or for both sections to slide independently. Also, it is contemplated that the first band and the second band may be arranged wherein they never actually overlap each other, but collapse to an abutting arrangement. Any of these arrangements will meet the concern of placing the occipital section of the collar beneath a patient's neck without disturbing or moving the patient.

The foregoing is considered as illustrative only of the principles of the invention. Furthermore, since numerous modifications and changes will readily occur to those skilled in the art, it is not desired to limit the invention to the exact construction and operation shown and described. While the preferred embodiment has been described, the details may be changed without departing from the invention, which is defined by the claims.

What is claimed is:

1. A method for immobilizing a trauma patient's neck and head, the steps consisting of:

providing an adjustable cervical collar, including an adjustable occipital section including a first band and a second band, whereby said second band lies substantially planar with respect to said first band, at least one slot having parallel, uninterrupted sides substantially throughout its length being formed in said first band, at least one stationary supporting post protruding from said second band and slidably receiving said slot, said slot being further formed with a constricted portion forming at least one biased end for retention of said post inside the biased end;

sliding said collar beneath said neck to resist movement of the head of the patient;

adjusting the height of the occipital section of the collar by moving said post toward and into said biased end so that the collar sufficiently supports the patient's neck while resisting movement of the head of the patient;

adjusting the mandibular section of the collar to support the patient's chin; and securing the occipital section to the mandibular section.

2. The method according to claim 1 wherein the collar may be slid beneath a patient's neck from either side of the patient's neck while resisting movement of the patient's neck and head.

3. An adjustable cervical collar for immobilizing the neck of a patient comprising:

an adjustable occipital section including a first band and a second band, said second band lying substantially planar with respect to said first band, at least one of said bands being movable relative to said other band, said first and second bands being independently positioned from one another, said occipital section being able to move unobstructedly from a retracted height to an extended height;

at least one post located on and protruding from said first band and at least one slot formed in said second band, said at least one slot receiving said post;

said at least one slot further including a constricted portion forming a biased end for restricting movement of said post into said slot when said post is nested within said biased end thereby fixedly positioning said bands; at said extended height;

at least one pull strap attached to and extending from said second band; and an adjustable fastener attached to one of said first and second bands for releasably encircling and fitting said collar to said neck.

4. An adjustable cervical collar for immobilizing the neck of a patient comprising:

an adjustable occipital section including a first band and a second band, whereby said second band lies substantially planar with respect to said first band;

at least one slot having parallel, uninterrupted sides substantially throughout its length, and being formed in said first band;

at least one stationary supporting post protruding from said second band and slidably receiving said slot;

said slot being further formed with a constricted portion forming at least one biased end for retention of said post inside the biased end for fixedly positioning at least one of said bands relative to the other of said bands;

at least one pull strap extending from said second band for manually adjusting the position of at least one of said bands relative to the other of said bands; and an adjustable fastener attached to one of said first and second bands for releasably encircling and fitting said collar to said neck.

5. The collar according to claim 3 further comprising a mandibular section.

6. The collar according to claim 5 wherein the mandibular section includes an adjustable chin support.

7. The collar according to claim 3 further comprising an elongated channel formed within the occipital section.

8. The collar according to claim 4 further comprising a mandibular section.

9. The collar according to claim 8 wherein the mandibular section includes an adjustable chin support.

10. The collar according to claim 4 further comprising an elongated channel formed within the occipital section.

* * * * *

UNITED STATES PATENT AND TRADEMARK OFFICE
CERTIFICATE OF CORRECTION

PATENT NO.    : 6,770,046 B2
DATED         : August 3, 2004
INVENTOR(S)   : Kyle J. Hansen It is certified that error appears in the above-identified patent and that said Letters Patent is hereby corrected as shown below:

Column 7,
Line 35, after "another," insert -- and --.

Column 8,
Line 2, after "bands" delete ";" (semi-colon).

Signed and Sealed this

Twenty-eighth Day of December, 2004

JON W. DUDAS
*Director of the United States Patent and Trademark Office*